United States Patent

Jahn et al.

Patent Number: 4,623,381
Date of Patent: Nov. 18, 1986

[54] PYRIDYL CONTAINING CYCLOHEXANE-1,3-DIONE DERIVATIVES AND HERBICIDAL USE

[75] Inventors: Dieter Jahn, Edingen-Neckarhausen; Rainer Becker, Bad Durkheim; Norbert Goetz, Worms; Michael Keil, Ludwigshafen; Bruno Wuerzer, Otterstadt, all of Fed. Rep. of Germany

[73] Assignee: BASF Aktiengesellschaft, Fed. Rep. of Germany

[21] Appl. No.: 521,661

[22] Filed: Aug. 10, 1983

[30] Foreign Application Priority Data

Aug. 13, 1982 [DE] Fed. Rep. of Germany ....... 3230087

[51] Int. Cl.⁴ .................. A01N 43/40; C07D 213/63; C07D 213/50
[52] U.S. Cl. ........................................ 71/94; 546/294; 546/296; 546/300; 546/333; 546/338
[58] Field of Search ............... 546/296, 333, 300, 338, 546/294; 71/94, 98, 90

[56] References Cited

U.S. PATENT DOCUMENTS

| | | | |
|---|---|---|---|
| 4,249,937 | 2/1981 | Iwataki et al. | 71/97 |
| 4,350,518 | 9/1982 | Sauter et al. | 71/88 |
| 4,376,646 | 3/1983 | Rohr et al. | 71/94 |
| 4,422,864 | 12/1983 | Becker et al. | 71/88 |

FOREIGN PATENT DOCUMENTS 3121355 12/1982 Fed. Rep. of Germany .
1461170 1/1977 United Kingdom .

OTHER PUBLICATIONS

Sawaki, et al, C.A. 85: 5281g.
Katritzky, et al., "The Principles of Heterocyclic Chemistry", (1968), pp. vii–xiv.
Morton, A. A., "The Chemistry of Heterocyclic Compounds", (1946), p. vii.

Primary Examiner—Henry R. Jiles
Assistant Examiner—Dale A. Bjorkman
Attorney, Agent, or Firm—Keil & Weinkauf

[57] ABSTRACT

Cyclohexane-1,3-dione derivatives of the formula

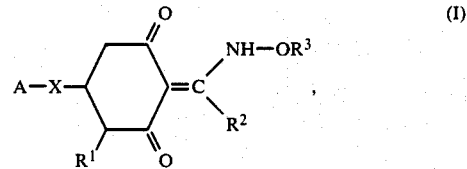

where $R^1$, $R^2$, $R^3$, A and X have the meanings given in the description, and their use for controlling undesirable plant growth.

6 Claims, No Drawings

PYRIDYL CONTAINING CYCLOHEXANE-1,3-DIONE DERIVATIVES AND HERBICIDAL USE

The present invention relates to cyclohexane-1,3-dione derivatives, herbicides which contain these compounds as active ingredients and methods of controlling undesirable plant growth with these compounds or herbicides containing them.

It has been disclosed that cyclohexane-1,3-dione derivatives can be used for controlling undesirable grasses in broad-leaved crops (British Pat. No. 1,461,170).

We have found that cyclohexane-1,3-dione derivatives of the formula

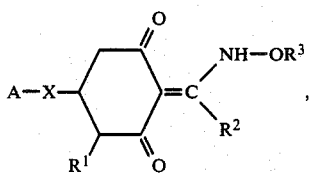

where A is a 4- to 7-membered heterocyclic structure which can contain not more than 4 heteroatoms from the group comprising O, S and N, and/or an oxo or thioxo group, can be unsubstituted for substituted by alkyl, alkoxy or phenyl and can be fused to an aromatic, X is an alkylene chain of not more than 5 carbon atoms or an alkenylene chain of not more than 5 carbon atoms and not more than 2 double bonds, which may or may not contain a sulfur or oxygen atom or a sulfinyl or sulfonyl group and is unsubstituted or substituted by not more than 2 alkyl groups or chlorine, with the proviso that X is not a pure saturated hydrocarbon chain if A is a non-aromatic heterocyclic radical containing not more than one double bond and 1 or 2 heteroatoms selected from the group comprising oxygen, nitrogen and sulfur, $R^1$ is hydrogen, methoxycarbonyl, ethoxycarbonyl, methyl or cyano, $R^2$ is alkyl of 1 to 4 carbon atoms and $R^3$ is alkyl of 1 to 3 carbon atoms, alkenyl of 3 or 4 carbon atoms, haloalkenyl of 3 or 4 carbon atoms and 1 to 3 halogen substituents, or propargyl, and salts of these compounds, possess herbicidal activity against grasses and cause little or no damage either to broad-leaved crop plants and monocotyledonous crops which do not belong to the family of the grasses (Gramineae) or, surprisingly, to cereals.

The compounds of the formula I can occur in several forms, all of which are embraced by the patent claims:

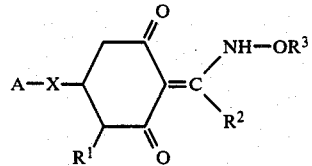

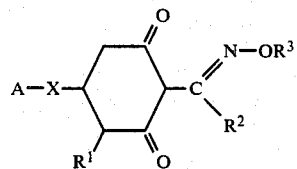

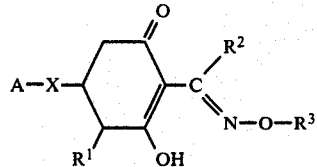

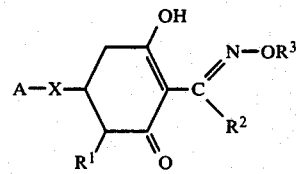

In formula I, A is a 4-membered to 7-membered heterocyclic structure which can contain not more than 4 heteroatoms selected from the group comprising O, S and N, and/or an oxo or thioxo group, and is unsubstituted or monosubstituted or polysubstituted by alkyl or alkoxy, each of 1 to 4 carbon atoms, or by phenyl, eg. furyl, thienyl, pyrrolyl, pyrazolyl, imidazolyl, triazolyl, tetrazolyl, oxazolyl, isoxazolyl, thiazolyl, pyridyl, pyrimidinyl, pyrazinyl, pyridazinyl, pyridonyl, tetrahydropyranyl, dihydropyranyl, thiazolinyl, thiadiazolinyl, dihydrothiopyranyl, dioxanyl, 5-methylfur-2-yl, 1-methylimidazol-2-yl, 3,5-dimethylpyrazolyl, 1-methyl-1,2,3,4-tetrazol-5-yl, 1-phenyl-1,2,3,4-tetrazol-5-yl, 3-methylisoxazol-5-yl, 4-methylthiazol-2-yl, 2-thioxo-5-methylthiadiazoline-3-yl, 1,3-dimethylindol-2-yl, 4,6-dimethylpyrimidin-2-yl, 4-methyltetrahydropyran-3-yl or 5,5-dimethyl-1,3-dioxan-2-yl. 5-membered and 6-membered heterocyclic structures are preferred.

The heterocyclic structures can also be fused to an aromatic, examples of such fused radicals being benzothiazolyl, benzoxazolyl, indolyl, benzopyrazolyl, benzoimidazolyl, benzotriazolyl, quinolyl, isoquinolyl, benzopyridazinyl, benzopyrimidinyl, benzopyrazinyl, benzofuryl and benzothienyl.

In formula I, X can be, for example, —CH$_2$—, —(CH$_2$)$_2$-, —CH(CH$_3$)—CH$_2$—, —CH$_2$—CH(CH$_3$)—, —CH=C(CH$_3$)—, —CH=C(i—C$_3$H$_4$)—, —CH$_2$—CH(i—C$_3$H$_7$)—, —CH=C(CH$_3$)—CH=C(CH$_3$)—C(CL)=C(CH$_3$)—, —CH$_2$—CH(CH$_3$)—CH$_2$—CH(CH$_3$)—, —CH$_2$-S-CH$_2$—, —S-CH$_2$—, —CH$_2$—S—CH(CH$_3$)—CH$_2$—, —S—CH(CH$_3$)—CH$_2$—, —CH$_2$—S—CH$_2$—CH$_2$—, —S—CH$_2$—CH$_2$—, —CH$_2$—S—CH$_2$—CH(CH$_3$)—, —S—CH$_2$—CH(CH$_3$)—, —CH$_2$—O—CH$_2$, —O—CH$_2$—, —CH$_2$—O—CH(CH$_3$)—, —O—CH(CH$_3$)—, —CH$_2$—O—CH(CH$_3$)—CH$_2$—, —O—CH(CH$_3$)—CH$_2$—, —CH$_2$—O—(CH$_2$)$_2$—, —O—(CH$_2$)$_2$—, —CH$_2$—O—CH$_2$—CH(CH$_3$)—, —O—CH$_2$—CH(CH$_3$)—, —CH$_2$—O—(CH$_2$)$_3$— or —O—(CH$_2$)$_3$—, $R^2$ is straight-chain or branched alkyl or 1 to 4 carbon atoms, ie. methyl, ethyl, n-propyl, i-propyl, n-butyl, sec.-butyl, i-butyl or tert.-butyl, and $R^3$ is propargyl, alkyl of 1 to 3 carbon atoms, alkenyl of 3 or 4 carbon atoms or haloalkenyl of 3 or 4 carbon atoms and no more than three halogen substituents, eg. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl, or 1,1,2-trichloroprop-1-en-3-yl.

Examples of salts of the compounds of the formula I are alkali metal salts, in particular potassium and sodium salts, alkaline earth metal salts, in particular calcium, magnesium and barium salts, and manganese, copper, zinc and iron salts as well as ammonium and phosphonium salts.

The compounds of the formula I can be obtained by reacting a compound of the formula

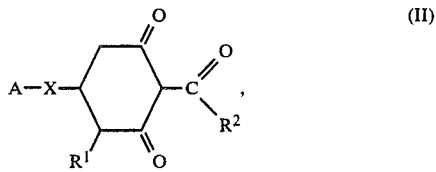

where A, X, $R^1$ and $R^2$ have the above meanings, with a hydroxylamine derivative $R^3O\text{-}NH_3Y$, where $R^3$ has the above meanings and Y is an anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction proceeds particularly readily at a pH of from 2 to 9, in particular from 4.5 to 5.5, which is advantageously obtained by the addition of an acetate, for example an alkali metal acetate, in particular sodium or potassium acetate, or a mixture of these two salts. Alkali metal acetates are added, for example, in amounts from 0.5 to 2 moles, based on the ammonium compound of the formula $R^3O\text{—}NH_3Y$.

Examples of suitable solvents are dimethylsulfoxide, alcohols, such as methanol, ethanol or isopropanol, benzene, hydrocarbons or chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting the mixture with a non-polar solvent, eg. methylene chloride, and distilling off the solvent under reduced pressure.

The compounds of the formula I can also be obtained by reacting a compound of the formula II with a hydroxylamine of the formula $R^3O\text{—}NH_2$, where $R^3$ has the above meanings, in an inert diluent at from 0° C. to the boiling point of the reaction mixture, in particular from 15° to 70° C. The hydroxylamine can, if appropriate, be used as an aqueous solution.

Examples of suitable solvents for this reaction are alcohols, such as methanol, ethanol, isopropanol or cyclohexanol, hydrocarbons or chlorohydrocarbons, such as hexane, cyclohexane or methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol or acetone. It is also possible to use a sodium alcoholate or a potassium alcoholate as the base.

The other metal salts, eg. the manganese, copper, zinc, iron, calcium, magnesium and barium salts, can be prepared from the sodium salts by reaction with the corresponding metal chlorides in aqueous solution. Ammonium and phosphonium salts can be prepared by reacting a compound of the formula I with ammonium hydroxide or phosphonium hydroxide, if appropriate in aqueous solution.

The compounds of the formula II can be prepared by a conventional method (Tetrahedron Lett. 29 (1975), 2491) from cyclohexane-1,3-diones of the formula III, which can also occur in the tautomeric forms IIIa and IIIb.

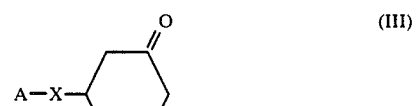

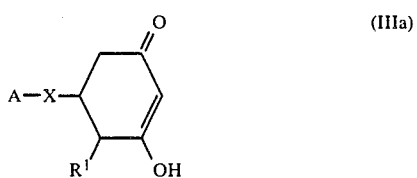

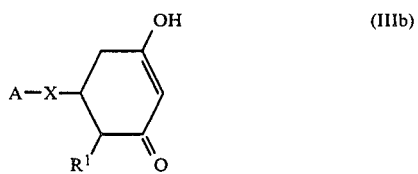

It is also possible to prepare compounds of the formula II via the enol-ester intermediates, which are obtained, possibly as isomer mixtures, in the conversion of compounds of the formula II, and undergo rearrangement in the presence of an imidazole or pyridine derivative (Japanese Preliminary Published Application 79/063,052).

The compounds of the formula III are obtained by a conventional process, as shown in the following equations:

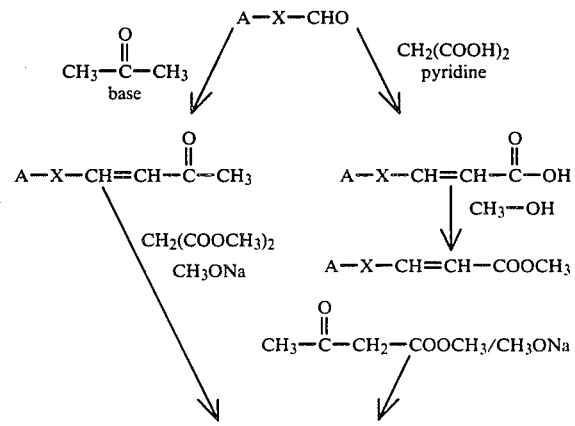

-continued

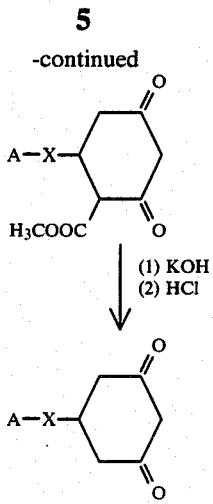

(1) KOH
(2) HCl

The aldehydes of the formula A-X-CHO are likewise obtainable by a conventional method, for example by reduction of the corresponding esters or nitriles, oxidation of alcohols, cleavage of acetals or addition reactions with α,β-unsaturated aldehydes.

In the Examples which follow, and illustrate the preparation of the cyclohexane-1,3-dione derivatives of the formula I, parts by weight bear the same relation to parts by volume as that of the kilogram to the liter.

EXAMPLE 1

5.0 parts by weight of 2-butyryl-5-(2-fur-2-yl-methylthio-n-propyl)-cyclohexane-1,3-dione, 1.5 parts by weight of ethoxyammonium chloride and 1.3 parts by weight of anhydrous sodium acetate in 70 parts by volume of ethanol were stirred for 12 hours at room temperature. The solvent was distilled off under reduced pressure, the residue was stirred with 100 parts by volume of water and 100 parts by volume of methylene chloride, the organic phase was separated off and the aqueous phase was extracted with 70 parts by volume of methylene chloride. The combined organic phases were washed with dilute hydrochloric acid and with water, dried over sodium sulfate and evaporated down under reduced pressure to give 2-(1-ethoxyaminobutylidene)-5-[2-(fur-2-ylmethylthio)-n-propyl]-cyclohexane-1,3-dione of $n_D^{31} = 1.5366$ and of the formula

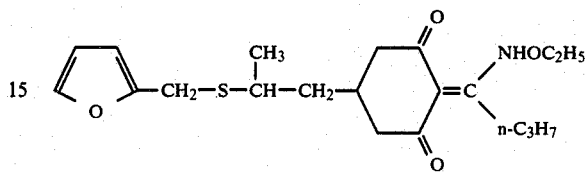

$C_{20}H_{29}NO_4S$ (380): calculated: C 63.30; H 7.70; N 3.69; S 8.45; found: C 63.6; H 7.6; N 3.9; S 8.2

EXAMPLE 2

10 parts by weight of 2-butyryl-5-[2-(3,5-dimethyl-pyrazol-1-yl)-ethyl]-cyclohexane-1,3-dione and 2.5 parts by weight of allyloxyamine in 100 parts by volume of ethanol were stirred for 12 hours at room temperature. The mixture was worked up by a method similar to that described in Example 1. 8.8 parts by weight of 2-(1-allyloxyaminobutylidene)-5-[2-(3,5-dimethyl-pyrazol-1-yl)-ethyl]-cyclohexane-1,3-dione of $n_D^{28} = 1.5329$ were obtained (Compound No. 2).

The compounds below are obtained in the same manner:

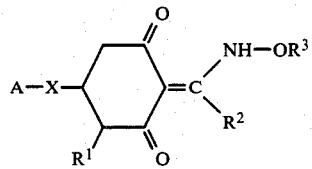

| Compound no. | A | X | $R^1$ | $R^2$ | $R^3$ | Physical data |
|---|---|---|---|---|---|---|
| 3 | 3,5-dimethyl pyrazol-1-yl | —CH$_2$—CH$_2$— | H | n-propyl | ethyl | $n_D^{28} = 1.5302$ |
| 4 | 3,5-dimethyl pyrazol-1-yl | " | H | " | —CH$_2$—CH=CHCl | $n_D^{32} = 1.5392$ |
| 5 | 3,5-dimethyl pyrazol-1-yl | " | H | " | n-propyl | $n_D^{32} = 1.5210$ |
| 6 | 3,5-dimethyl pyrazol-1-yl | " | H | " | propargyl | $n_D^{32} = 1.5370$ |
| 7 | 3,5-dimethyl pyrazol-1-yl | " | H | " | methyl | $n_D^{32} = 1.5297$ |
| 8 | pyrazol-1-yl | " | H | " | ethyl | $n_D^{21} = 1.5321$ |
| 9 | " | " | H | " | allyl | $n_D^{21} = 1.5370$ |
| 10 | fur-2-yl | —CH=CH— | H | " | " | $n_D^{31} = 1.5605$ |
| 11 | " | " | H | " | ethyl | $n_D^{31} = 1.5525$ |
| 12 | " | —CH=C(CH$_3$)— | H | " | " | $n_D^{22} = 1.5608$ |
| 13 | " | " | H | " | allyl | $n_D^{22} = 1.5683$ |
| 14 | imidazol-1-yl | —CH(CH$_3$)CH$_2$— | H | ethyl | " | |
| 15 | " | " | H | " | ethyl | |
| 16 | 1,2,4-triazol-1-yl | " | H | n-propyl | " | $n_D^{36} = 1.5067$ |
| 17 | " | " | H | " | allyl | |
| 18 | " | " | H | ethyl | ethyl | |
| 19 | " | " | H | " | allyl | |
| 20 | pyrid-3-yl | —CH=C(CH$_3$)— | H | n-propyl | " | $n_D^{27} = 1.5706$ |
| 21 | " | " | H | " | ethyl | $n_D^{27} = 1.5662$ |
| 22 | " | " | H | " | propargyl | $n_D^{27} = 1.5780$ |
| 23 | " | " | H | " | —CH$_2$—CH=CHCl | |

-continued

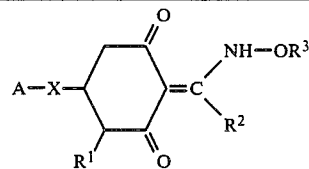

| Compound no. | A | X | R¹ | R² | R³ | Physical data |
|---|---|---|---|---|---|---|
| 24 | " | —CH=C(CH₃)—CH=C(CH₃)— | H | " | ethyl | $n_D^{36} = 1.5743$ |
| 25 | " | " | H | " | allyl | $n_D^{36} = 1.5725$ |
| 26 | tetrahydropyran-3-yl | —CH=C(CH₃)— | COOCH₃ | " | allyl | |
| 27 | " | " | COOCH₃ | " | ethyl | |
| 28 | " | " | COOCH₃ | " | " | $n_D^{26} = 1.523$ |
| 29 | " | " | H | " | allyl | $n_D^{26} = 1.529$ |
| 30 | " | " | H | " | —CH₂—CH=CHCl | |
| 31 | 5,6-dihydro-2H—pyran-3-yl | " | H | " | ethyl | |
| 32 | 5,6-dihydro-2H—pyran-3-yl | " | H | " | allyl | |
| 33 | tetrahydropyran-2-yl | —CH₂—O—CH(CH₃)— | H | " | " | |
| 34 | " | " | H | " | ethyl | |
| 35 | 5,6-dihydro-2H—thiopyran-3-yl | —CH=C(CH₃)— | H | " | " | |
| 36 | 5,6-dihydro-2H—thiopyran-3-yl | " | H | " | allyl | |
| 37 | 5,6-dihydro-2H—thiopyranyl | " | H | " | propargyl | |
| 38 | 2-thiono-5-methyl-1,3,4-thiadiazolin-3-yl | —CH(CH₃)—CH₂— | H | " | allyl | m.p.: 114–118° C. |
| 39 | 2-thiono-5-methyl-1,3,4-thiadiazolin-3-yl | " | H | " | ethyl | m.p.: 114–118° C. |
| 40 | 4,5-dihydrothiazol-2-yl | —S—CH(CH₃)—CH₂— | H | " | " | m.p.: 98° C. |
| 41 | " | " | H | " | allyl | m.p.: 120° C. |
| 42 | 1-phenyltetrazol-5-yl | " | H | " | " | |
| 43 | " | " | H | " | " | |
| 44 | 1-methyltetrazol-5-yl | " | H | " | " | |
| 45 | " | " | H | " | " | |
| 46 | 3-methylisoxazol-5-yl | —CH₂—O—CH(CH₃)— | H | " | " | $n_D^{23} = 1.5238$ |
| 47 | " | " | H | " | ethyl | $n_D^{23} = 1.5192$ |
| 48 | " | " | COOCH₃ | " | " | $n_D^{23} = 1.5119$ |
| 49 | 2-methylthiazol-4-yl | " | H | " | " | |
| 50 | " | " | H | " | allyl | |
| 51 | " | —CH₂—O—CH(CH₃)—CH₂— | H | " | " | |
| 52 | " | " | H | " | ethyl | |
| 53 | pyrid-2-yl | —S—CH(CH₃)—CH₂— | H | " | " | $n_D^{30} = 1.5562$ |
| 54 | " | " | H | " | allyl | |
| 55 | 4,6-dimethyl-pyrimidin-2-yl | " | H | " | " | |
| 56 | 4,6-dimethyl-pyrimidin-2-yl | " | H | " | ethyl | m.p.: 53–59° C. |
| 57 | 4,6-dimethyl-pyrimidin-2-yl | —S—CH₂—CH₂— | COOCH₃ | ethyl | " | $n_D^{30} = 1.5567$ |
| 58 | 4,6-dimethyl-pyrimidin-2-yl | " | COOCH₃ | " | allyl | $n_D^{30} = 1.5560$ |
| 59 | 4,6-dimethyl-pyrimidin-2-yl | " | H | " | " | $n_D^{24} = 1.5640$ |
| 60 | 4,6-dimethyl-pyrimidin-2-yl | " | H | " | ethyl | m.p.: 58–62° C. |
| 61 | 5,5-dimethyl-1,3-dioxan-2-yl | —CCl=C(CH₃)— | H | n-propyl | " | |
| 62 | 5,5-dimethyl-1,3-dioxan-2-yl | " | H | " | allyl | |
| 63 | benzthiazol-2-yl | —S—CH₂—CH₂— | H | " | " | |
| 64 | " | " | H | " | ethyl | $n_D^{24} = 1.606$ |
| 65 | benzoxazol-2-yl | " | H | " | " | $n_D^{26} = 1.580$ |
| 66 | " | " | H | " | allyl | |
| 67 | 1,3-dimethylindol-2-yl | —CH₂— | H | " | ethyl | m.p.: 99–102° C. |
| 68 | " | " | H | " | allyl | |
| 69 | 4,6-dimethylpyrimidin-2-yl | —S—CH₂—CH₂— | CN | ethyl | " | $n_D^{29} = 1.5683$ |
| 70 | 4,6-dimethylpyrimidin-2-yl | " | CN | " | ethyl | $n_D^{30} = 1.5641$ |
| 71 | fur-2-yl | —CH=C(CH₃)— | H | n-propyl | propyl | m.p.: 56–57° C. |
| 72 | " | " | H | " | propargyl | $n_D^{27} = 1.5699$ |
| 73 | " | " | H | " | —CH₂—CH=CHCl | $n_D^{27} = 1.5708$ |
| 74 | pyrid-4-yl | " | H | " | ethyl | |
| 75 | " | " | H | " | allyl | $n_D^{26} = 1.570$ |
| 76 | thien-2-yl | " | H | " | " | $n_D^{26} = 1.584$ |

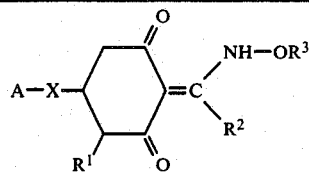

| Compound no. | A | X | R¹ | R² | R³ | Physical data |
|---|---|---|---|---|---|---|
| 77 | " | " | H | " | ethyl | $n_D^{26} = 1.582$ |
| 78 | " | " | H | " | —CH₂—CH=CHCl | $n_D^{26} = 1.588$ |
| 79 | " | " | H | " | methyl | m.p.: 73° C. |
| 80 | " | " | H | " | —CH₂—C≡CH | |
| 81 | " | " | H | " | n-propyl | m.p.: 44° C. |
| 82 | " | —CH=C(i-C₃H₇)— | H | " | ethyl | |
| 83 | pyrid-4-yl | —CH₂—CH(CH₃)— | H | " | " | |
| 84 | " | " | H | " | allyl | |
| 85 | pyrid-3-yl | " | H | " | " | |
| 86 | " | " | H | " | ethyl | |
| 87 | pyrid-2-yl | " | H | " | " | |
| 88 | " | " | H | " | allyl | |
| 89 | 4,6-dimethyl-pyrimidin-2-yl | —S—CH₂—CH₂— | H | ethyl | ethyl | |
| 90 | 4,6-dimethyl-pyrimidin-2-yl | " | H | " | allyl | |

¹H-NMR-spectroscopic data: chemical shift in δ values (ppm) in CDCl₃, based on tetramethylsilane as internal standard. Abbreviations for signal structures:

s=singlet
d=doublet
q=quartet
m=multiplet

| Compound no. | | | |
|---|---|---|---|
| 46 | 4.1 (q) | 2.25 (s) | |
| 47 | 4.5 (d) | 2.23 (s) | |
| 48 | 4.1 (q) | 2.30 (s) | |
| 61 | 4.12 (q) | 1.88 (s) | |
| 62 | 4.55 (d) | 1.88 (s) | |
| 64 | 4.15 (q) | 3.43 (t) | 7.9 (d) |
| 65 | 4.10 (q) | 1.58 (q) | 7.30 (m) |
| 74 | 4.15 (q) | 1.92 (s) | 6.3 (s) |
| 76 | 4.50 (d) | 1.95 (s) | 6.47 (s) |
| 80 | 4.65 (m) | 1.90 (s) | 6.95 (m) |
| 82 | 4.12 (q) | 1.0 (d) | |

The cyclohexanedione derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

Examples of formulations follow.

I. 90 parts by weight of compound No. 1 is mixed with 10 parts by weight of N-methyl-alpha-pyrrolidone. A mixture is obtained which is suitable for application in the form of very fine drops.

II. 10 parts by weight of compound No. 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound No. 8 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound No. 9 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound No. 3 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound No. 13 is intimately mixed with 95 parts by weight of particulate kaolin. A dust is obtained containing 5% by weight of the active ingredient.

VII. 30 parts by weight of compound No. 46 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound No. 47 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents may be applied pre- or postemergence. Preferably, the novel active ingredients or agents containing them are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved, and the growth stage of the plants, and varies from 0.05 to 5 kg/ha, but is preferably from 0.1 to 2.0 kg/ha.

The action of the novel cyclohexane-1,3-dione derivatives of the formula I on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to active the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean and bush bean plants used for the postemergence treatment were grown in a peat-enriched substrate. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were either 0.125 or 0.25 kg of active ingredient per hectare.

The pots were set up in the greenhouse—species from warmer areas at from 20° to 35° C., and species from moderate climates at 10° to 25° C. The experiments were run for 2 to 4 weeks. During this period, the plants were tended and their reactions to be various treatments assessed. The scale used for assessment was 0 to 100, 0 denoting no damage or normal emergence, and 100 denoting nonemergence or complete destruction of at least the visible plant parts.

The plants used in the greenhouse experiments were *Alopecurus myosuroides, Avena fatua, Beta vulgaris, Echinochloa crus-galli, Glycine max., Gossypium hirsutum, Lolium multiflorum, Setaria faberii, Sorghum halepense, Triticum aestivum,* and *Setaria italica.*

On preemergence application, for example compounds 1, 2, 9, 11, 12, 13, 20, 48 and 61, applied at a rate of 3.0 kg/ha, had a very good herbicidal action on grassy species.

On postemergence application, for instance compound No. 21 combated, at 0.25 kg/ha, unwanted plants without damaging the broadleaved crop plants, and compound No. 47, at 0.125 kg/ha, selectively damaged unwanted grasses in wheat.

In view of the good tolerance of the herbicides according to the invention, or agents containing them, by numerous broadleaved and other crops, and the numerous application methods possible, they may be used in a large number of crops for removing unwanted wild grasses or grassy crop plants growing where they are not desired.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Petroselinum crispum spp tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum dochna | |
| Spinacia oleracea | spinach |
| Theobroma cacao | cacao plants |

-continued

| Botanical name | Common name |
| --- | --- |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the cyclohexane-1,3-dione derivatives of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenyl-carbamates, thiolcarbamates, halocarboxylic acids, triazines, amides, ureas, diphenyl ethers, triazinones, uracils, benzofuran derivatives, etc.

It may also be useful to apply the novel compounds, either on their own or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexane-1,3-dione derivative of the formula

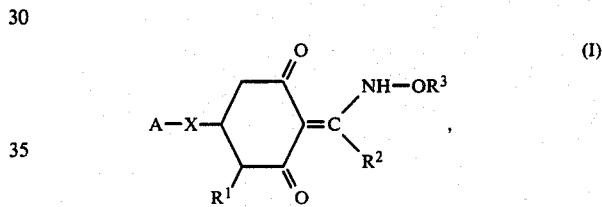

where A is pyridyl which can be unsubstituted or substituted by alkyl, alkoxy or phenyl, X is an alkylene chain of not more than 5 carbon atoms or an alkenylene chain of not more than 5 carbon atoms, but not vinyl, and note more than 2 double bonds, which may or may not contain a sulfur or oxygen atom or a sulfinyl or sulfonyl group and is unsubstituted or substituted by not more than 2 alkyl groups or chlorine, $R^1$ is hydrogen, methoxycarbonyl, ethoxycarbonyl, methyl or cyano, $R^2$ is alkyl of 1 to 4 carbon atoms and $R^3$ is alkyl of 1 to 3 carbon atoms, alkenyl of 3 to 4 carbon atoms, haloalkenyl of 3 to 4 carbon atoms and 1 to 3 halogen substituents, or propargyl, or a salt thereof.

2. A cyclohexane-1,3-dione derivative of the formula I as defined in claim 1, wherein the alkylene or alkenylene chain of X contains sulfur, oxygen, sulfinyl or a sulfonyl group.

3. 2-Allyloxyaminobutylidene-5-[1-methyl-2-(pyrid-3-yl)-vinyl]-cyclohexane-1,3-dione.

4. A herbicidal composition consisting essentially of inert additives and a herbicidally effective amount of a cyclohexane-1,3-dione derivative of formula I as claimed in claim 1.

5. A herbicidal composition consisting essentially of inert additives and from 0.1 to 95 wt% of a cyclohexane-1,3-dione derivative of formula I as claimed in claim 1.

6. A method for combating the growth of grasses, wherein the grasses and/or the area to be kept free from unwanted plant growth are treated with a herbicidally effective amount of a cyclohexane-1,3-dione derivative of formula I as claimed in claim 1.

* * * * *